United States Patent
Perdices et al.

(10) Patent No.: US 7,109,384 B2
(45) Date of Patent: Sep. 19, 2006

(54) PROCESS TO EXTRACT PHENOLIC COMPOUNDS FROM A RESIDUAL PLANT MATERIAL USING A HYDROTHERMAL TREATMENT

(75) Inventors: Mercedes Ballesteros Perdices, Madrid (ES); Maria Jose Negro Alvarez, Madrid (ES); Paloma Manzanares Secades, Madrid (ES); Ignacio Ballesteros Perdices, Madrid (ES); Jose Miguel Oliva Dominguez, Madrid (ES)

(73) Assignee: Centro de Investigaciones Energeticas, Medioambientales Y Technologicas, Madrid (ES)

( * ) Notice: Subject to any disclaimer, the term of this patent is extended or adjusted under 35 U.S.C. 154(b) by 294 days.

(21) Appl. No.: 10/801,511

(22) PCT Filed: Feb. 20, 2003

(86) PCT No.: PCT/ES03/00085

§ 371 (c)(1),
(2), (4) Date: Mar. 16, 2004

(87) PCT Pub. No.: WO2004/009206

PCT Pub. Date: Jan. 29, 2004

(65) Prior Publication Data

US 2004/0176647 A1    Sep. 9, 2004

(30) Foreign Application Priority Data

Jul. 17, 2002    (ES) ............................... 200201671

(51) Int. Cl.
*C07C 37/68* (2006.01)
(52) U.S. Cl. ..................................................... 568/749
(58) Field of Classification Search ................. 568/749
See application file for complete search history.

(56) References Cited

OTHER PUBLICATIONS

Ballersteros et al, Ethanol Production from Olive Oil Extraction Residue Pretreated with Hot Water, Human Press, Spring 2002; 98-100, pp. 717-732.*
Alonso-Salces et al; Pressurized Liquid Etraction for the Determination of Polyphenols in Apple; Journal of Chromatography A, Nov. 9, 2001, vol. 933, pp. 37-43.*

* cited by examiner

*Primary Examiner*—Samuel Barts
*Assistant Examiner*—Kellette Gale
(74) *Attorney, Agent, or Firm*—John C. McMahon

(57) ABSTRACT

The hydrothermal treatment is based on placing the crude residual plant material in contact with hot water in a closed reactor, comprising the following steps:
  a) placing the material to be treated in contact with water in a closed reactor, and adjusting the solid/liquid ratio so that it ranges from 1/5 to 1/15 (w/v):
  b) stirring;
  c) heating to a temperature between 180 and 240° C., and at a pressure so that the water is maintained in liquid phase;
  d) constantly stirring the mixture for a time period between 4 and 30 minutes; and
  e) cooling the reactor to approximately 40° C., unloading the mixture, filtering and recovering the liquid fraction.

6 Claims, 1 Drawing Sheet

PROCESS TO EXTRACT PHENOLIC COMPOUNDS FROM A RESIDUAL PLANT MATERIAL USING A HYDROTHERMAL TREATMENT

"This application is a 371 of ES/2003/000085, filed Feb. 20, 2003."

OBJECT AND FIELD OF THE INVENTION

The present invention relates to a process to extract phenolic compounds mainly present in crude residual plant materials, in particular in the crude residue from the two-phase olive oil production process, called "alpeorujo" by the use of a hydrothermal treatment, particularly a treatment that uses hot water in liquid phase. By applying this treatment, the hydroxytyrosol and tyrosol present in the alpeorujo are extracted so their content can be determined. These compounds have an important added value as antioxidants in the food and pharmaceutical industry.

BACKGROUND OF THE INVENTION

Currently, the olive oil extraction system according to a two-phase extraction process [J. Alba, F. Hidalgo, $M^a$ A Ruiz, F. Martínez, $M^a$ J. Moyano, A. Cert, $M^a$ C. Pérez and $M^a$ V Ruiz. "Características de los aceites de oliva de primera y segunda centrifugación" *Grasas y Aceites* 47, (1996) 163–181] has substantially reduced the volume of wastes produced with the traditional three-phase system which requires the supplementary addition of water. Nevertheless, there is still a high quantity (approximately 2,600,000 tons/year in Spain) produced of a residue, called two-phase pomace or "alpeorujo", formed by the pulp, the pit and the vegetable water. The depleted product, with a fat content lower than 1% and a humidity around 65%, is an inconvenient and very abundant residue (around 80% of the ground olive), impossible to store in the olive-oil mill. Due to the environmental, economic and social problems caused by the large quantity of sub-product generated, it is necessary to find solutions for a comprehensive treatment thereof, which is feasible from an economic point of view and does not negatively affect the environment.

The reuse of this sub-product in the conventional olive-pomace oil extractors for an additional extraction of the remaining oil contained therein, poses a difficult problem associated with its characteristics of having a paste consistency and a high content in sugars and fine solids, which make its use as such very difficult in conventional olive-pomace drying systems. Although several investigations are being performed to optimize the drying process from an operational and energy-saving point of view [R. Arjona, A. García and P. Ollero. "The drying of alpeorujo, a waste product of the olive mill industry", *Journal of Food Engineering* 41 (1999) 229–234], the high energy cost of the humidity reduction phase is a clear drawback from the economic point of view. Another alternative treatment to reduce the volume of this residue, such as its incineration in combustion plants, also requires the prior drying of the material and may also imply a series of environmental problems related to the emission of toxic exhaust gases. In this regard, it would be necessary to use suitable gas cleaning systems, which would substantially increase the overall economic cost of the process.

The alpeorujo contains all the sugars and other soluble substances that are dissolved in the vegetable water of the conventional olive oil extraction process. Thus, there is a possibility of revaluating this residue by the production of products of high added value therefrom, which would mean an improvement in the management of sub-products from the olive-producing industry, whilst permitting the use of a cheap source of raw materials for products of industrial interest. An example of this approximation to the revaluation of alpeorujo is in patent application ES 2060 549, which discloses a process to produce mannitol and products derived from alpeorujo, by processes of diluting, filtration, decanting or centrifuging.

In addition to compounds such as mannitol, the majority of the polyphenols present in the olive pulp and pit are found in this sub-product, for which reason it may constitute a suitable source of natural phenolic antioxidants. The phenolic compounds of the olive pulp have been extensively researched given their importance in fruit processing. The most abundant glycoside in olive pulp, oleuropein, is formed by the heterosidic ester of elenolic acid and hydroxytyrosol and is what gives olives their bitter taste. Oleuropein is very abundant in the green fruit and their percentage is quantitatively reduced on reaching maturity. Ligustroside and verbascoside are also present in the pulp. In the pit, the described glycosides are similar to the above and of the ligustroside type, of which tyrosol instead of hydroxytyrosol forms a part.

The most abundant phenolic compounds in alpeorujo are tyrosol and hydroxytyrosol, together with p-coumaric, caffeic, ferulic and vanillic acids in less quantity. The hydroxytyrosol mainly comes from the oleuropein of the fruit, which is hydrolysed by means of an esterase present therein during the olive grinding. These polyphenols, which are mainly present in the fruit, but also in less quantity in the leaves, flowers and other plant organs, are natural antioxidant compounds, which perform various functions. In a recent study, their antioxidant effect has been proven as they block the process in the initiation phase, either oxidizing themselves by forming more stable natural peroxidic compounds, or acting on the already formed radicals to prevent the propagation phase. On the one hand, the phenols present in the olive protect the oil from degrading [Gutfinger, T. "Polyphenols in olive oils" *J. Am. Oil Chem Soc.* 58 (1981) 966–7], and they have infinite potent biological actions on the human metabolism, which have been studied in vitro. The most important of them is the inhibition of low-density lipoprotein (LDL) oxidation, which constitutes an essential phase within the atherogenic process. However, phenolic compounds also have important free-radical scavenging activity [F. Visioli, G. Bellomo, C. Galli. "Free radical-scavenging properties of olive oil polyphenols". *Biochem Biophys Res. Municipality* 247 (1998) 60–64] against the production of the superoxide anion and hypochlorous acid, which means they act as protection against oxygen free radicals and their toxic effects and, therefore, prevent cellular aging and tumours [R. W Owen, A. Giacosa, W. E Hull, R. Haubner, B. Spiegelhalder, H. Bartsch. "The antioxidant/anticancer potential of phenolic compounds isolated from olive oil" *Eur. J. Cancer* 36(10), (2000) 1235–1247], they protect against heart disease and are closely related to the benefits attributable to the consumption of olive oil in the Mediterranean diet. Some of them, such as hydroxytyrosol, are potent inhibitors of platelet aggregation and thromboxane generation and counteract the production of the potent pro-inflammatory agent leukotriene B4.

The high potential for these phenolic compounds in the pharmaceutical and food industry has caused a growing interest in the last few years in their production from olive leaves and fruit for various applications. For example, the Japanese patent application JP08119825 discloses the application of the hydroxytyrosol obtained from olive oil extraction as an active component in cutaneous formulations for skin treatments. The patent application WO 00/36936 discloses the preparation of food compositions which have increased levels of phenolic compounds from olive oil to improve their nutritional qualities. The patent U.S. Pat. No. 6,165,475 relates to the use of oleuropein in various medical or agricultural applications, as well as a method to prepare an aqueous extract rich in this compound which comes from the fruit. Nevertheless, there are almost no references on the use of plant materials, such as the pulp, that remain after the extraction of the untreated olive oil (crude), as a substrate for the recovery of polyphenols, the use of this crude substrate forming one of the novel aspects of the present invention. A work published by the applicants for the production of bioethanol from alpeorujo [I. Ballesteros, J. M Oliva, M. J. Negro, P. Manzanares, M. Ballesteros. "Ethanol production from olive oil extraction residue pretreated with hot water" *Applied Biochemistry and Biotechnology*, 98–100 (2002) 717–732], discloses that, after a hydrothermal treatment performed to promote the subsequent transformation of the cellulose contained in the substrate to ethanol, phenolic compounds are obtained such as those disclosed in the present application. However, the residue used in said work has undergone a washing and drying process before being used with the aim of promoting the subsequent fermentation process to which it is subjected. Surprisingly, the applicants have now found that the use of this substrate when crude, i.e. as it is received from the olive-mill, without undergoing any prior washing and drying treatment, is advantageous in a process to extract phenolic compounds as is disclosed in this application. Firstly, the use of crude alpeorujo avoids the expense of water in the washing phase and the subsequent generation of a liquid residue, whose management may be problematic from an environmental point of view. Furthermore, it is a clear advantage from an energy-saving point of view as it avoids the drying phase, after that of the washing, which is disclosed in the aforementioned work. Finally, as it uses the crude substrate, a higher yield of hydroxytyrosol and tyrosol are obtained than that corresponding to the same substrate after being washed and dried.

As regards the extraction methods of the phenolic compounds mainly present in the leaves and the fruit, these vary depending on the type of starting material. Thus, polyphenol extraction methods with organic solvents such as methanol/water have been disclosed to extract from fruit [D. Ryan, H. Lawrence, P. Prenzier, M. Antolovich, K. Robards. "Recovery of phenolic compounds from *Olea europaea*" *Analytica Chimica Acta* 445 (2001), 67–77], alcohol to extract from leaves (patent U.S. Pat. No. 5,714,150) and ether/ethyl acetate [A. D. Bianco, I. Muzzalupo, A. Piperno, G. Romeo, N. Uccella. "Bioactive derivatives of oleuropein from olive fruits" *J. Agric. Food Chem.* 47 (1999), 3531–3534] or methanol [F. Angeroso, N. D'Alessandro, Konstantinou. P., L. Di Giacinto. "GL-LC evaluation of phenolic compounds in virgin olive oil" *J. Agric. Food. Chem.* 43 (1995), 1802–1807] applied to polyphenol extraction from olive oil L. Lesage-Meessen et al., [L. Lesage-Meessen, D. Navarro, S. Maunier, J-C Sigoillot, J. Lorquin, M. Delattre. J-L Simon, M. Asther and M. Labat. "Simple phenolic content in olive oil residues as a function of extraction systems" *Food Chemistry* 75(4) (2001) 501–507, disclose the extraction of tyrosol and hydroxytyrosol from the residue obtained from olive oil using ethyl acetate, permitting the recovery of around 30% of the total amount of phenols present in the residue. However, all these methods have the drawback of their high cost as regards the use of solvents and the generation of wastes which are difficult to eliminate.

The patent WO 01/45514 discloses a method to extract antioxidant compositions from the fruit and olive oil extraction sub-products, in a multi-phase process that uses several aqueous and/or polar extractions and solid matrixes which is considerably more complex than the present application. The Spanish patent application ES 2143939 discloses the use of a steam explosion process to recover the structural phenolic components from the olive pits and the kernel shell. With this process, the materials are treated in a 2 1 steam explosion unit at temperatures around 200° C. for time periods of 2–4 minutes, there then occurring an abrupt decompression and the subsequent unloading of the reactor. The results obtained show that hydroxytyrosol is extracted from the pit in soluble extract concentrations of up to 1% in dry weight of the pit, less quantity than that obtained in the pulp, where this polyphenol is mainly found. In the case of the kernel shells, tyrosol is obtained in concentrations of up to 0.5% in dry weight and it is verified that the addition of acid to the material before the treatment appreciably increases the quantities of phenols detected in the soluble extract.

The object of the present invention is to extract the phenolic derivatives present in crude residual plant materials, in particular, in the residue remaining after olive oil extraction by a two-phase centrifugation process (alpeorujo), using a hydrothermal treatment that uses water at a high temperature and at a pressure to keep the water in liquid phase.

In the sense used in this description, the term "crude residual plant materials" includes residues of plant origin which contain phenolic derivatives, in particular phenolic derivatives of industrial interest, such as alpeorujo, olive pit debris, olive kernel shell, corncob residues, etc, which have not undergone, prior to their use, any washing and/or drying process.

As is used in this description, phenolic derivatives of industrial interest include the phenols tyrosol and hydroxytyrosol.

In the present invention, a hydrothermal treatment is used, which uses hot water in liquid phase, to extract phenolic derivatives from the crude olive oil extraction residue. This application of treatment with hot water to the recovery of phenolic compounds, is a new use thereof which, up to the present time, has basically been used as a pre-treatment of lignocellulosic materials prior to an enzymatic hydrolysis of the cellulose to glucose, as disclosed in the patent U.S. Pat. No. 5,846,787. This treatment, in the case of crude alpeorujo, is an advantage to the aforementioned extraction methods as it allows the recovery of phenols of interest without the exogenous addition of solvents or acids, which means the overall process is more economic and gives less quantity of residues to eliminate.

The method of extraction by hydrothermal treatment of this invention is based on subjecting the material to be treated to a treatment with hot water, at a temperature of 180 to 240° C., in an closed autoclave-type reactor, at a pressure that permits maintaining the water in liquid phase, during an appropriate time period, of 4 to 30 minutes, with the aim of solubilizing the phenolic derivatives, mainly present in said material. Next, the liquid fraction is recovered by filtration and its phenol concentration is determined. During the treatment of the substrate of the present invention, an autohydrolysis of the hemicellulosic debris occurs in said pulp residue that produces the liberation of acetyl groups and, in consequence, a reduction in the pH of the liquid fraction, thus promoting the solubilization of the phenols of interest. Once the phenolic derivatives have been extracted, their concentration in the aqueous extracts is determined by high performance liquid chromatography (HPLC) techniques or gas chromatography-mass spectometry (GC-MS) or spectroscopy techniques, which are well known by those skilled in the art.

DESCRIPTION OF THE INVENTION

The present invention relates to a process to extract phenolic compounds present in crude residual plant materials, in particular the crude residue from the two-phase olive oil production process, called "alpeorujo", by the use of a hydrothermal treatment which uses hot water in liquid phase. The crude residual material is treated in an autoclave-type reactor at a temperature between 180 and 240° C. for an appropriate time period, maintaining, during this time, the water in liquid phase by applying suitable pressure. Next, the reactor is cooled, the humid material is filtered and the tyrosol and hydroxytyrosol content of the liquid fraction is determined. Using this treatment, one can obtain an aqueous extract with a content of up to 1.9% (w/w) of hydroxytyrosol and 0.7% (w/w) of tyrosol, from which the compounds of interest can be obtained by conventional extraction/purification techniques.

The application of the hydrothermal treatment to the recovery of soluble phenols is one of the novel aspects of this invention, and an advantage in relation to the methods disclosed in the art, as it does not use solvents and/or acids, nor do abrupt depressurizations occur as in the steam explosion treatment. Furthermore, the use of a residual plant material, whose elimination could become a problem, as a substrate, means a clear advantage from an environmental and residue management point of view. In addition, the use of this material in its crude state means new advantages from the economic and environmental point of view in relation to the previously washed and dried material, while permitting an increase in the yield of the extracted phenolic compounds.

BRIEF DESCRIPTION OF THE DRAWINGS

To complement the previous description and with the object of helping towards a better understanding of the characteristics of the invention, a detailed description of a preferred embodiment will be made, based on a set of drawings which is attached to this specification and wherein the following is represented with an illustrative, non-limiting character.

DETAILED DESCRIPTION OF THE INVENTION

Figure 1:
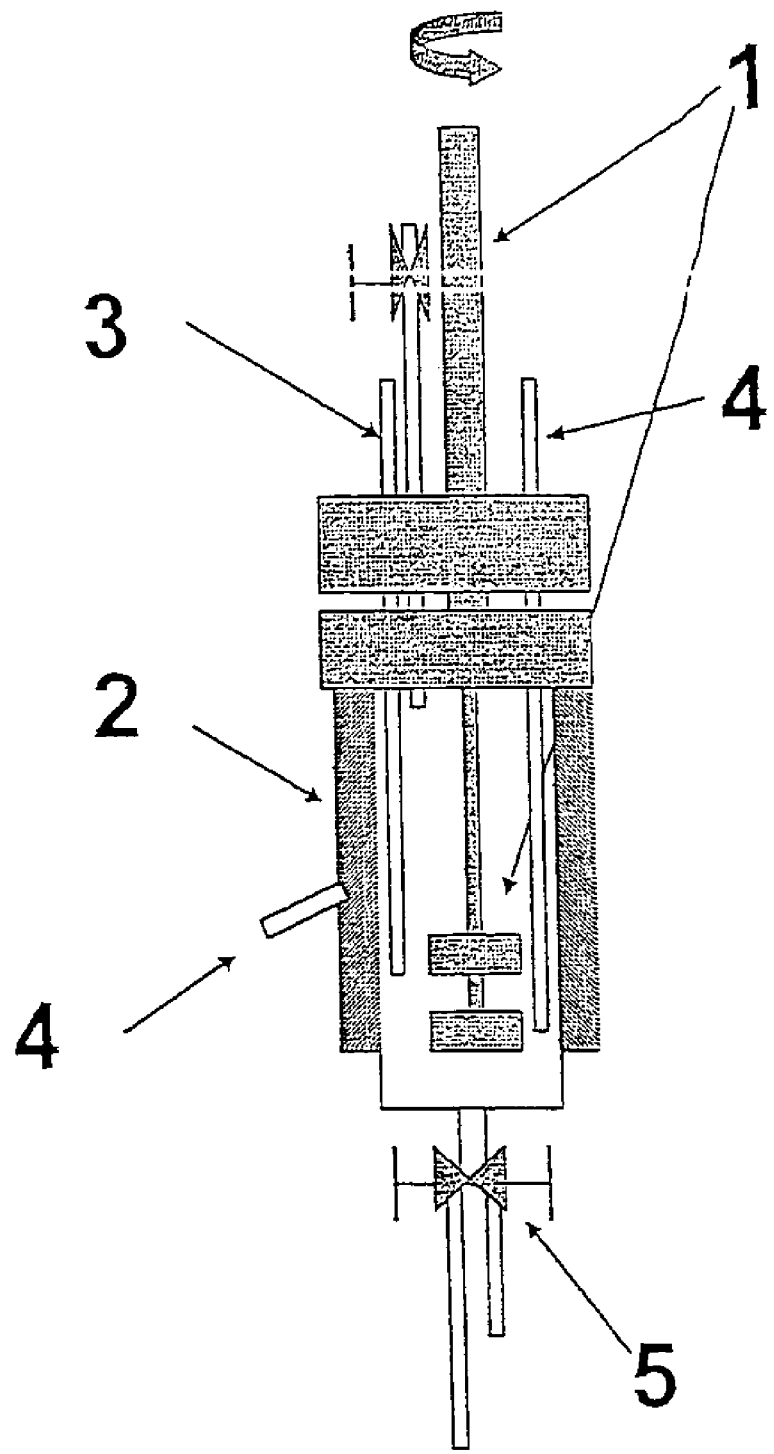
FIG. 1 shows a schematic diagram of the autoclave-type reactor, with stirring, which has been used in the embodiment of the process object of the present invention.

The starting material used in the particular embodiment of the present invention is the crude residue from olive oil extraction using a two-phase centrifugation process, called alpeorujo, which contains debris of the pulp, the pit and vegetable water.

The reactor used in the present invention can be any reactor designed to be pressurized at pressures so that the water at a temperature of 180–240° C. is maintained in liquid phase. In a particular embodiment, a stainless steel autoclave-type reactor has been used, equipped with a resistor and magnetic stirring, with a temperature and stirring rate control (FIG. 1). A condenser coil-type refrigeration unit is attached around the reactor to cool the reactor once the treatment time has concluded. This type of reactors are available in several sizes, from 60 to 1000 ml and the water temperature can reach from 100° C. to 600° C. A preferred temperature for the embodiment of the process object of this invention is that between 180° C. and 240° C. The maximum pressure in the reactor may reach from 4.5 to 22.4 MPa, depending in the reactor volume and the heating temperature selected. The heating rate is 2.5–3° C./minute. The residence time of the substrate in the reactor until the treatment temperature is reached is from 60 to 90 minutes. Once the treatment temperature has been reached inside the reactor, the period of treatment time to the selected temperature is variable, typically between 4 and 30 minutes in those conditions.

The substrate is introduced in the reactor at room temperature (from 15 to 25° C.), and water is added until reaching a proportion that permits having a final solid/liquid ratio in the reactor of between 1/5 and 1/15, e.g. 1/12. The stirrer rate is established so that a complete aqueous mixture is attained, preferably from 400 to 700 rpm. The treatment temperature is set and once this is reached, the previously established treatment time begins to be counted. Once the treatment has concluded, the heating jacket is removed from the reactor and cold water is loaded around the condenser coil. The temperature of the reactor contents lower to 130° C. in approximately 2 minutes. The reactor remains closed and the mixtures is stirred until the temperature lowers to approximately 40° C. The reactor is then opened, the material unloaded and filtered. The tyrosol and hydroxytyrosol content is determined by standard high performance liquid chromatography (HPLC) techniques.

EXAMPLE 1

The material used in this example is crude residual alpeorujo from a two-phase olive oil production process, provided by the company Oleica el Tejar S. C. L. (Cordoba, Spain), from which the main fraction of residual pit had been separated.

Firstly, a sample of the crude pulp was taken and its solid content was calculated by drying in a stove at 105° C. until constant weight. The aforementioned material used in this example has a solid percentage of 30% (w/w).

A stainless steel autoclave-type reactor, model EZE-Seal (Autoclave Engineers, Erie, Pa.), 500 ml volume, with a nominal capacity of 400 ml, is used. According to the use disclosed in the present invention, the reactor is opened and 160 g of crude substrate (48 g of dry weight according to the previously calculated percentage) and water until 400 ml, is introduced at room temperature. The rate of the stirrer (1) is set at 600 rpm. The heating jacket (2) is positioned and the treatment temperature is set at 225° C. The reactor begins to be heated and once the selected temperature is reached, a period of treatment of the substrate begins of 4 minutes. Once this time has passed, the heating is disconnected and the heating jacket (2) is removed. Next, water is passed through the condenser coil (3) and the mixture is left to cool as it is stirred in the closed reactor, until the thermocouple (4) connected to the reactor shows a temperature of approximately 40° C. The reactor is opened and the treated substrate is unloaded through an outlet (5).

The substrate is filtered and the tyrosol and hydroxytyrosol content is determined by HPLC in a Hewlett-Packard (Palo Alto, Calif.) unit, equipped with a detector with a diode array. The chromatographic separation is performed with a Bio-Rad Aminex HPX-87H stainless steel column (Hercules, Calif.) using sulphuric acid and acetonitrile (82/18, v/v) as an eluent. The compounds of interest are identified by their retention time and absorption spectrum in the optical density range of 200–320 nm. The quantification is performed using tyrosol standards, available in Sigma (St. Louis, Mo.) and oleuropein supplied by Extrasynthese (Genay, France), The hydroxytyrosol standard was obtained from oleuropein by acid hydrolysis, as disclosed by E. Graciani and A. Vázquez ["A Study of the poplar compounds in olive oil by high performance liquid chromatography (HLPC). Cromatography in inverse phase". *Grasas y Aceites* 31 (1980) 237–243].

The results obtained show a hydroxytyrosol and tyrosol content in the liquid fraction of 1.85% and 0.6% (on dry weight of pulp), respectively.

The invention claimed is:

1. A process to extract phenolic compounds from a crude residual plant material using a hydrothermal treatment, characterized in that it places said crude residual plant material in contact with hot water in a closed reactor, at a temperature between 180° C. and 240° C., and a pressure so that the water is maintained in liquid phase.

2. The process according to claim 1, characterized in that said crude residual plant material is selected from the residues of the olive oil production process, such as pits, kernel shells, alpeorujo and mixtures thereof.

3. The process according to claim 1, characterized in that said reactor is an autoclave-type stirred reactor.

4. The process according to any of claims 1, 2 or 3, characterized in that it comprises the steps of:
   a) adding the crude residual plant material to the reactor and adjusting the solid/liquid ratio in the reactor with water, so that it ranges from 1/5 to 1/15 (w/v);
   b) stirring;
   c) heating to a temperature between 180 and 240° C., and at a pressure so that the water is maintained in liquid phase;
   d) constantly stirring the mixture for a time period between 4 and 30 minutes; and
   e) cooling the reactor to approximately 40° C., unloading the mixture, filtering and recovering the liquid fraction.

5. The process according to claim 4, characterized in that the phenolic compounds extracted are tyrosol and hydroxytyrosol.

6. The process according to claim 5, characterized in that the tyrosol and hydroxytyrosol content is determined by standard HPLC techniques.

* * * * *